United States Patent

Coe et al.

[11] Patent Number: 5,583,137
[45] Date of Patent: Dec. 10, 1996

[54] HETEROCYCLIC COMPOUNDS FOR ENHANCING ANTITUMOR ACTIVITY

[75] Inventors: Jotham W. Coe, East Lyme; Anton F. J. Fliri, Norwich; Takushi Kaneko, Guilford; Eric R. Larson, Stonington, all of Conn.

[73] Assignee: Pfizer Inc., New York, N.Y.

[21] Appl. No.: 284,655

[22] PCT Filed: Nov. 17, 1992

[86] PCT No.: PCT/US92/09554

§ 371 Date: Aug. 17, 1994

§ 102(e) Date: Aug. 17, 1994

[87] PCT Pub. No.: WO93/17021

PCT Pub. Date: Sep. 2, 1993

[51] Int. Cl.$^6$ ............ C07D 473/16; C07D 495/04; A61K 31/505
[52] U.S. Cl. ............ 514/261; 514/266; 544/250; 544/277; 544/278
[58] Field of Search ............ 544/277; 514/261, 514/266

[56] References Cited

FOREIGN PATENT DOCUMENTS 404356  12/1990  European Pat. Off. .
404355  12/1990  European Pat. Off. .

OTHER PUBLICATIONS

Fojo, Cancer Res. 45, 3002–7 (1985).
Tsuruo in "Xenobiotics and Cancer", pp. 241–251 (1991).
Gottesman, J. Biol. Chem., 263, p. 12163 (1988).
Mmardanov, Chem. Abs., 84, 85431 (1975).
Bellamy, Cancer Inves., 8, 547 (1990).
Kaneko, Current Opinion in Therapeutic Patents, p. 1043 (Jul. 1991).
Hochhauser, Brit. Med. Bull. 47, pp. 178–196 (1991).

*Primary Examiner*—Mark L. Berch
*Attorney, Agent, or Firm*—Peter C. Richardson; Gregg C. Benson; John D. Conway

[57] ABSTRACT

2,6-Diaminopurines, 3,5-diamino-6,7,8,9-tetrahydrobenzo[b]thiophene[2,3-d]pyrimidines and 2,4-diaminothieno[3,2-d]pyrimidines useful as inhibitors of P-glycoproteins and potentiators of chemotherapeutic agents.

10 Claims, No Drawings

HETEROCYCLIC COMPOUNDS FOR ENHANCING ANTITUMOR ACTIVITY

This application is a 371 of PCT/US92/09554.

TECHNICAL FIELD

This invention relates to certain heterocyclic compounds and their use as sensitizers of tumor cells to anticancer agents.

BACKGROUND ART

In cancer chemotherapy the effectiveness of anticancer drugs is often limited by the resistance of tumor cells. Some tumors such as of the colon, pancreas, kidney and liver are generally innately resistant, and other responding tumors often develop resistance during the course of chemotherapy. The phenomena of multidrug resistance (MDR) is characterized by the tumor cells cross-resistance to adriamycin, daunomycin, vinblastine, vincristine, daxol, actinomycin D and etoposide. The resistance cells are often associated with overexpression of the mdrl gene. This gene product is a family of 140–220 kd trans-membrane phosphoglycoproteins (P-glycoprotein) which function as an ATP-dependent efflux pump. Thus, it has been postulated that this efflux mechanism keeps the intracellular level of the anticancer drug low, allowing the tumor cells to survive.

In recent years various substances such as verapamil, nifedipine and diltiazem have been used in in vitro experimental systems to reverse the MDR phenomena. More recently some of these agents have been tested clinically as MDR reversing agents. Little efficacy has been observed with verapamil or trifluoroperazine. Thus, there is a need for an effective MDR reversing agent.

2-Piperazino-4-morpholinothieno[3,2-d]pydmidines are reported in German Often. 2,055,085 [CA 77, 88539f (1972)].

Thienopyrimidines and pyridopyrimidines are claimed as gastric acid secretion inhibitors in European Patent Application 404,356 and 404,355, respectively.

DISCLOSURE OF THE INVENTION

The compounds of the present invention are of the formulae

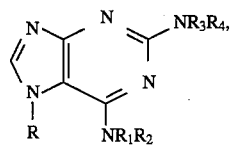   I

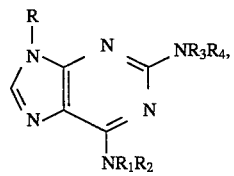   II

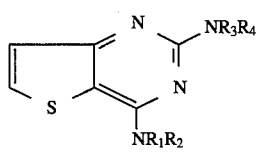   III or

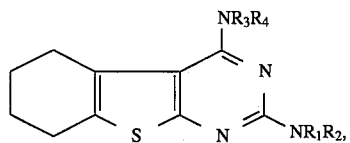   IV and a pharmaceutically acceptable acid addition salt thereof where R is hydrogen, alkyl of one to three carbon atoms or phenylalkyl of seven to ten carbon atoms; $R_1$ and $R_3$ are each hydrogen or alkyl of one to three carbon atoms; $R_2$ and $R_4$ are each aralkyl of the formula

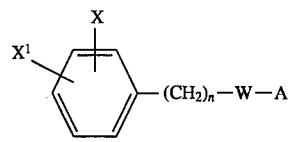

where X and $X^1$ are each hydrogen, alkyl of one to three carbon atoms, alkoxy of one to three carbon atoms, hydroxy, fluoro, chloro, trifluoromethyl, amino, alkylamino of one to three carbon atoms or dialkylamino of two to six carbon atoms, X and $X^1$ taken together are methylenedioxy or ethylenedioxy, n is an integer of 0 or 1, W is S, 0 or a chemical bond and A is alkylene of two to four carbon atoms; and $R_1$ and $R_2$ or $R_3$ and $R_4$ when taken together with the nitrogen to which they are attached each form a moiety of the formula

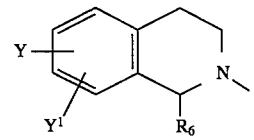

where $R_6$ is hydrogen, alkyl of one to three carbon atoms or dialkoxyphenylalkyl said alkoxy each of one to three carbon atoms and said alkyl of one to three carbon atoms and Y and $Y^1$ are each hydrogen, alkyl of one to three carbon atoms, alkoxy of one to three carbon atoms, fluoro, chloro, trifluoromethyl, amino, alkylamino of one to three carbon atoms or dialkylamino of two to six carbon atoms.

A preferred group of compounds are those of formula I, where R is phenylalkyl of seven to ten carbon atoms; $R_1$ and $R_2$ taken together with the nitrogen to which they are attached form a moiety of the formula

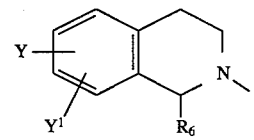

where $R_6$ is hydrogen and Y and $Y^1$ are each alkoxy of one to three carbon atoms; $R_3$ is hydrogen; and $R_4$ is aralkyl of the formula

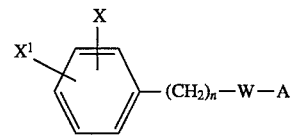

where X and $X^1$ are each alkoxy of one to three carbon atoms, n is 0, W is a chemical bond and A is ethylene.

Especially preferred within this group are the compounds where R is 1-phenylethyl; Y is 6-methoxy and $Y^1$ is 7-methoxy; and X is 3-methoxy and $X^1$ is 4-methoxy and where R is benzyl; Y is 6-methoxy and $Y^1$ is 7-methoxy; and X is 3-methoxy and $X^1$ is 4-methoxy.

A second group of preferred compounds are those of formula II where R is alkyl of one to three carbon atoms or phenylalkyl of seven to ten carbon atoms; $R_1$ and $R_2$ taken together with the nitrogen to which they are attached form a moiety of the formula

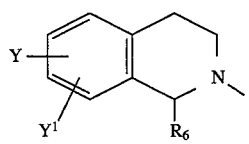

where $R_6$ is hydrogen or dialkoxyphenylalkyl said alkoxy each of one to three carbon atoms and said alkyl of one to three carbon atoms and Y and $Y^1$ are each alkoxy of one to three carbon atoms; $R_3$ is hydrogen; and $R_4$ is aralkyl of the formula

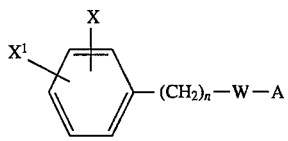

where X and $X^1$ are each alkoxy of one to three carbon atoms, n is 0, W is a chemical bond and A is ethylene. Especially preferred within this group are the compounds where R is 1-phenylethyl; $R_6$ is hydrogen, Y is 6-methoxy and $Y^1$ is 7-methoxy; and X is 3-methoxy and $X^1$ is 4-methoxy, where R is benzyl; $R_6$ is 3,4-dimethoxybenzyl, Y is 6-methoxy and $Y^1$ is 7-methoxy; and X is 3-methoxy and $X^1$ is 4-methoxy and where R is methyl; $R_6$ is 3,4-dimethoxybenzyl, Y is 6-methoxy and $Y^1$ is 7-methoxy; and X is 3-methoxy and $X^1$ is 4-methoxy.

A third group of preferred compounds are those of formula III wherein $R_1$ and $R_2$ taken together with the nitrogen to which they are attached form a moiety of the formula

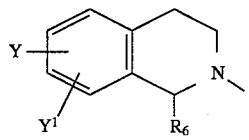

where $R_6$ is hydrogen and Y and $Y^1$ are each alkoxy of one to three carbon atoms; $R_3$ is hydrogen; and $R_4$ is aralkyl of the formula

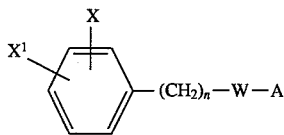

where X and $X^1$ are each alkoxy of one to three carbon atoms, n is 0, W is a chemical bond and A is ethylene. Especially preferred within this group is the compound where Y is 6-methoxy and $Y^1$ is 7-methoxy; and X is 3-methoxy and $X^1$ is 4-methoxy.

The present invention also includes a method of inhibiting a P-glycoprotein in a mammal in need of such treatment which comprises administering to said mammal a P-glycoprotein inhibiting amount of a compound of formulae I-IV. Preferred is the method where the mammal is a human suffering from cancer and said compound is administered before, with or after the administration to said human of an anticancer effective amount of a chemotherapeutic agent.

Also included is a pharmaceutical composition for administration to a mammal which comprises a P-glycoprotein inhibiting amount of a compound of formulae I-IV, a pharmaceutically acceptable carrier and, optionally, an anticancer effective amount of a chemotherapeutic agent.

As previously indicated, the compounds of formulae I-IV form pharmaceutically acceptable acid addition salts. Said pharmaceutically acceptable acid addition salts include, but are not limited to, those with HCl, HBr, $HNO_3$, $H_2SO_4$, $H_3PO_4$, $CH_3SO_3H$, $C_6H_5SO_3H$, $CH_3CO_2H$, gluconic acid, tartaric acid, maleic acid and succinic acid. In the case of those compounds of the formulae I-IV which contain a further basic nitrogen, it will, of course, be possible to form diacid addition salts (e.g., the dihydrochloride) as well as the usual monoacid addition salt.

As one skilled in the art recognizes, compounds of formulae I-IV have the potential for containing asymmetric carbon atoms. All these potential isomers are considered within the scope of the present invention.

DETAILED DESCRIPTION

Compounds of the present invention are prepared by reacting a 2,6-dichloropurine, 3,5-dichlorothieno[2,3-d]pyrimidine or 2,4-dichlorothieno[3,2-d]pyrimidine with the requisite amine, $R_1R_2NH$.

In a more detailed description of the procedure, one molar amount of the dichloro compound and one molar amount of the amine, $R_1R_2NH$, as the hydrochloride salt are reacted in a water immiscible solvent, such as methylene chloride, containing two molar amounts of a tertiary amine, such as triethylamine. The reaction is usually complete in 3–24 hours when conducted at room temperature.

The 6-chloro group of the 2,6-dichloropurine is the more reactive while the 5- and 4-chloro substituents of the thieno [2,3-d]pyrimidine and thieno[3,2-d]pyrimidine are, respectively, the most reactive.

On completion of the reaction, the reaction mixture is quenched in water and the product isolated by concentration of the water immiscible solvent. Purification of the product can be carried out by recrystallization or column chromatography.

Alternately, the reaction can be carried out in a water miscible solvent, such as dimethylacetamide. In such cases the reaction mixture, on completion, is added to water and the product filtered or extracted.

The isolated intermediate is then reacted with the requisite amine, $R_3R_4$,NH, in a reaction-inert solvent. In practice, one mole of the mono-chloro compound is reacted with one mole of amine, $R_3R_4$,NH, in a highly polar solvent such as 2-(2-ethoxyethoxy)ethanol containing one mole of a high boiling amine, such as diisopropylethylamine. The reaction temperature is 160°–170° C. with a reaction time of about 72 hours.

The reaction mixture is cooled to room temperature, diluted with methylene chloride and chromatographed on silica gel. The isolated product is converted to an appropriate salt, for example the hydrochloride salt, by adding it to a methanolic solution of hydrogen chloride. Further purification can be carried out by recrystallization.

Generation of the free base from an acid addition salt can readily be carried out by treating an aqueous solution or suspension of the salt with at least one equivalent of an organic or inorganic base followed by extraction of the free base product with a water immiscible solvent such as ethyl acetate or methylene chloride. Removal of the solvent gives the desired base.

Compounds of formulae I-IV are inhibitors of the functions of P-glycoprotein, particularly human mdr 1 protein or P-glycoprotein related and membrane associate proteins which are participating in the transport of xenobiotics or proteins across membranes e.g., cell membranes of eukariotic and proeukariotic origin e.g., pmfdr, however not exclusive or restricted to these examples.

Compounds included in general formulae I-IV are useful in combination chemotherapy of cancer, malaria, viral infections such as AIDS, in therapy of septic shock syndrome or inflammation and may be useful in enhancing of the xenobiotics limited due to the presence of P-glycoprotein or P-glycoprotein related functional proteins. Compounds of formulae I-IV increase the activity/efficacy of adriamycin, daunomycin, etoposide, epipodophyllotoxin congeners, actinomycin D, emetin, daxol, vincristine, vinblastine, chloroquine, antracycline antibiotics and of drugs which are structurally and functionally related to the above mentioned examples, in particular, when the activity of these drugs has been shown to be limited due to the presence and function of P-glycoprotein, e.g. human mdr 1 protein or P-glycoprotein related proteins.

The compounds of the present invention are evaluated as potentiators of chemotherapeutic agents using a Cellular Drug Retention Assay. This assay was designed to study the effect of compounds on cellular retention of radiolabeled drug. In this case 14C-adriamycin retention by multidrug resistant human carcinoma cells, KBV1, is measured.

KBV1 cells are routinely grown in tissue culture as monolayers in DMEM high glucose medium containing 1 ug/ml vinblastine, 10% heat inactivated fetal calf serum and supplemented with Glutamine, Pen-strep and Garamycin.

The assay protocol (described below) should be applicable with minor modifications, to a wide variety of cell lines grown in tissue culture.

Assay Protocol:

(1) Seed replicate 6-well tissue culture plates with 1.2× 10E6 cells per 2 ml per well in absence of Vinblastine;

(2) Incubate 24 hours at 37 degrees in humidified incubator (5% CO2);

(3) Aspirate off the spent media and overlay monolayers with 2 ml/well of fresh medium that is 2 uM in Adriamycin (2 uM unlabeled Adriamycin+20000 cpm of 14C-Adr) and the test agent at concentrations varying from 0 to 100 uM;

(4) Following incubation for 3 hours at 37 degrees in humidified incubator, remove media and wash monolayers twice with 2 ml of ice cold buffered saline;

(5) Detach monolayers using 0,5 ml of trypsin/EDTA, collect detached cells and transfer to scintillation vial. Rinse wells once with 0.5 ml of buffered saline and add to same vial containing cells;

(6) Add 5 ml of Beckman Ready-Safe scintillation fluid to vial, vortex and determine radioactivity per sample using a scintillation counter (10 minutes per sample);

(7) For background control: pre-incubate monolayers at 4 degrees for 15 minutes then remove media and add fresh ice-cold media containing Adr (see step 3). Following incubation for 3 hours at 4 degrees remove media and wash monolayers twice with 2 ml ice-cold buffered saline, then proceed as in step 5;

(8) Results are expressed as T/C and ED3x values as defined below:

T/C=pmoles Adr per 10E6 cells treated with test agent/

ED3x =concentration of test agent that produces a 3 fold increase in cellular accumulation of radiolabeled Adr, i.e. T/C =3.

Calculation

Specific cpm=[sample cpm—background cpm]

Specific activity=[cpm/total conc. of Adr]

pmoles Adr=[specific cpm/specific activity]

pmoles Adr per 10E6 cells=[(pmoles Adr per well/number of cells per well)×10E6 cells]

As previously mentioned, compounds of the present invention and salts thereof are useful in potentiating the anticancer effects of chemotherapeutic agents. Such agents can include adriamycin, daunomycin, aclacinomycin A, actinomycin C, actinomycin D, mithramycin, vinblastine, maytansine, bruceantin, homoharintonin, anguindin, neocarcinostatin, mitomycin C and anthramycin.

The compounds of the present invention can be administered with, 24 hours before or up to 72 hours after the administration of the chemotherapeutic agents. When administered with said agents, they can be taken either separately or coadministered in the same formulation.

The compounds of the present invention whether taken separately or in combination with an anti-cancer agent, are generally administered in the form of pharmaceutical compositions comprising at least one of the compounds of formulae I-IV and optionally a chemotherapeutic agent, together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelation and, for parenteral administration, in the form of injectable solutions of suspensions, and the like.

For use in the potentiation of anticancer agents in a mammal, including man, a compound of formulae I-IV is given in an amount of about 0.5–100 mg/kg/day, in single or divided doses. A more preferred dosage range is 2–50 mg/kg/day, although in particular cases, at the discretion of the attending physician, doses outside the broader range may be required. The preferred route of administration is generally oral, but parenteral administration (e.g. intramuscular, intravenous, intradermal) will be preferred in special cases, e.g., where oral absorption is impaired as by disease or where the patient is unable to swallow.

The present invention is illustrated by the following examples, but is not limited to the details or scope thereof.

EXAMPLE 1

2-(3,4-Dimethoxyphenethylamino)-6-( 1,2,3,4-tetrahydro-6,7-dimethoxyquinol-2-yl)purine hydrochloride A. 2-chloro-6-(1,2,3,4-tetrahydro-6,7-dimethoxyisoquinol-2-yl)purine A mixture of 5.67 g of 2,6-dichloropurine, 6.89 g of 1,2,3,4-tetrahydroisoquinoline hydrochloride and 6 g of triethylamine in 40 ml of dimethylacetamide was stirred under a nitrogen atmosphere at room temperature for 3.5 hours. The mixture was poured into 500 ml of water and stirred for 30 minutes. The solids were filtered, washed with water, pressed dry and stirred in hot methanol for 1 hour. The suspension was filtered while hot and the solids dried, 9.85 g (95% yield), m.p. 271°–276° C. dec.

B. 2-(3,4-dimethoxyphenethylamino)-6-(1,2,3,4-tetrahydro-6,7-dimethoxyisoquinol-2yl)purine hydrochloride A mixture of 692 mg of the product of Example 1A, 362 mg of 3,4-dimethylphenethylamine and 258 mg of diisopropylethylamine in 6 ml of 2-(2-ethoxyethoxy)ethanol was stirred under a nitrogen atmosphere at 165° C. for 5 hours. The reaction mixture was cooled, diluted with chloroform and the solids filtered. The flitrate was loaded on 90 g of silica gel/chloroform and eluted with 2% methanol chloroform. The fractions containing the product were combined and concentrated to dryness, 84 mg. Treatment of the residue with 1N hydrogen chloride in methanol followed by recrystallization from methanol gave 61 mg of the desired product, m.p. 1.52°–154° C.

EXAMPLE 2

2-(3,4-Dimethoxyphenethylamino)-6-(1,2,3,4-tetrahydro-6,7-dimethoxyisoquinol-2-yl)-9-methylpurine hydrochloride  A.  2-chloro-6-(1,2,3,4-tetrahydro-7-dimethoxyisoauinol-2-yl)-9-methylpurine A suspension of 1.76 g of the product of Example 1A, 930 mg of potassium carbonate and 950 mg of methyl iodide in 100 ml of dimethylsulfoxide was warmed until the purine was dissolved. The reaction was cooled to room temperature and stirred overnight. The mixture was poured over ice, the pH adjusted to 5 with acetic acid and the product extracted with methylene chloride. The extract was washed with water, dried over sodium sulfate and concentrated in vacuo to a yellow oil. The residue was chromatographed on silica gel using from 0% methanol in chloroform to 2% methanol in chloroform (V:V). The fractions containing the product were combined and concentrated to dryness. The residual foam was triturated with methanol to give 2.09 g of the desired product, m.p. 182°–184° C. B. 2-(3,4-dimethoxyphenethylamino)-6-(1,2,3,4-tetrahydro-6,7-dimethoxyisoquinol-2-yl)-9-methylpurine hydrochloride Following the procedure of Example 1B and starting with 1.44 g of the product of Example 2A, 724 mg of 3,4-dimethoxyphenethylamine and 516 mg of diisopropylethylamine in 2 g of 2-(2-ethoxyethoxy)ethanol gave 115 mg of the desired product, m.p. 179°–181° C.

EXAMPLE 3–9

Employing the procedure of Example 1B and starting with the appropriate reagents, the following compounds were prepared:

2-(3,4-dimethoxyphenethylamino)-6-(1,2,3,4-tetrahydro-6,7-dimethoxyisoquinol-2-yl)-9-benzylpurine hydrochloride, m.p. 152°–154° C.;

2-(3,4-dimethoxyphenethylaminol)-6-(1,2,3,4-tetrahydro-6,7-dimethoxyisoquinol-2-yl)-7-benzylpurine hydrochloride, m.p. 139°–141 ° C.;

2-(3,4-dimethoxyphenethylamino)-6-(1,2,3,4-tetrahydro-6,7-dimethoxyisoquinol-2-yl )-7-methylaminopurine hydrochloride, m.p. 159°–164° C.;

2-(3,4-dimethoxyphenethylamino)-6-(1,2,3,4-tetrahydro-6,7-dimethoxyisoquinol-2-yl)-7-(1-phenylamino)purine hydrochloride, m.p. 128°–132° C.;

2-(3,4-dimethoxyphenethylamino)-6-(1,2,3,4-tetrahydro-6,7-dimethoxyisoquinol-2-yl)-9-(1-phenylethylamino)purine hydrochloride, m.p. 108°–114° C.;

2-(3,4-dimethoxyphenethytamino)-6-(1,2,3,4-tetrahydro-1-[3,4-dimethoxybenzyl]-6,7 -dimethoxyisoquinole-2-yl)-7-benzylpurine hydrochloride, m.p. 139°–141° C.;

2-(3,4-dimethoxyphenethylamino)-6-(1,2,3,4-tetrahydro-1-[3,4-dimethoxybenzyl]-6,7-dimethoxyisoquinol-2-yl)-9-methylpurine hydrochloride, m.p. 148°–150° C.

EXAMPLE 10

2-(3,4-Dimethoxyphenethylamino )-4-(1,2,3,4-tetrahydro-6,7-dimethoxyisoquinol-2-yl)thieno[3,2-d]pyrimidine hydrochloride
A. 2-chloro-4-1,2,3,4-tetrahydro-6,7-dimethoxyisoquinol-2-yl)thieno[3,2-d]pyrimidine A mixture of 1.381 g of 2,4-dichlorothieno[3,2-d]pyrimidine, 1.55 g of 1,2,3,4-tetrahydro-6,7-dimethoxyisoquinoline hydrochloride and 1.41 g of triethylamine in 40 ml of dimethylacetamide was stirred at room temperature for 72 hours. The reaction mixture was poured into 300 ml of water and the solids filtered, dried and recrystallized from methanol, 1.7 g, m.p. 173°–175° C.

B. 2-(3,4-dimethoxyphenethylamino)-4-(1,2,3,4-tetrahydro-6,7-dimethoxyisoquinol-2-yl)thiene [3,2-d]pyrimidine hydrochloride A mixture of 1.08 g of the product of Example 8A, 543 mg of 3,4-dimethoxyphenethylamine and 387 mg of diisopropylethylamine in 1.25 g of 2-(2-ethoxyethoxy)ethanol was stirred at 170° C. for 24 hours under nitrogen. The reaction was cooled to room temperature and diluted with 5 ml of chloroform. The resulting solution was chromatographed on silica gel using from 0% methanol in chloroform to 2% methanol in chloroform as the eluent. The fractions containing the product were combined and concentrated to an orange oil. Treatment of the oil with 15 ml of a 1N solution of hydrogen chloride in methanol gave 1.04 g of the desired product, m.p. 210°–212° C.

EXAMPLE 11

3-(3,4-Dimethoxyphenethylamino)-5-(1,2,3,4-tetrahydro-6,7-dimethoxyisoquinol-2-yl)-6,7,8,9-tetrahydrobenzenethieno[2,3-d]pyrimide hydrochloride
3-chloro-5-(1,2,3,4-tetrahydro-6,7-dimethoxyisoquinol-2-yl) 6,7,8,9-tetrahydrobenzothieno[2,3-d]pyrimidine A solution of 623 mg of 3,5-dichloro-6,7,8,9-tetrahydrobenzothieno[2,3d]pyrimidine, 554 mg of 1,2,3,4-tetrahydro-6,7-dimethoxyisoquinoline hydrochloride and 4 ml of triethylamine in 40 ml of methylene chloride was stirred at room temperature under nitrogen for 15 hours. An additional 275 mg of the appropriate tetrahydroisoquinoline hydrochloride and 1 ml of triethylamine were added and stirring continued for an additional 9 hours. The reaction mixture was diluted with 100 ml of methylene chloride and extracted with 1N hydrochloric acid (3×75 ml), water (1×75 ml) and a brine solution (1×75 ml). The organic phase was dried over sodium sulfate and concentrated to an oil. The residue oil was dissolved in methanol and the resulting precipitated solids filtered and dried, 740 mg0 m.p. 158°–160° C.

3-(3,4-dimethoxyphenethylamino)-5-(1,2,3,4-tetrahydro-6,7-dimethoxyisoquinol-2-yl)-6,7,8,9-tetrahydrobenzothieno[2,3-d]hydrochloride hydrochloride A solution of 666 mg of the product of Example 9A, 290 mg of 3,4-dimethoxyphenethylamine and 206 mg of diisopropylethylamine in 800 mg of 2-(2-ethoxyethoxy)ethanol was heated a170° C. under nitrogen for 24 hours. The reaction mixture was cooled to room temperature, diluted with 3 ml of chloroform and chromatographed on 40 g of silica gel using chloroform as the eluent. The fractions containing the product were combined. concentrated in vacuo and the residue chromatographed on 25 g of silica gel in an 45 cm (18 inch) by 25 mm column using chloroform as the eluent and collecting 6 ml fractions. Fractions 9–20 were combined, concentrated and the residue added to 1N methanolic hydrogen chloride. The solids were filtered and dried, 211 mg, m.p. 195°–198° C.

PREPARATION A 2,6-Dichloro-7-benzylpurine and 2,6-dichloro-9-benzylpurine

To a suspension of 4.56 potassium carbonate and 5.67 g of 2,6-dichloropurine in 40 ml of dimethylsulfoxide was added, 5.64 g of benzylbromide. The mixture was stirred for 45 minutes under nitrogen at room temperature and was then poured onto crushed ice. The pH of the mixture was adjusted to 5 with acetic acid and extracted with methylene chloride (2×400 ml). The combined extracts were washed with water (6×400 ml), and brine (1×400 ml), dried over sodium sulfate and evaporated. The residue was chromatographed on silica gel using chloroform-methanol (9:1-V:V) as the eluent to give 3.59 g of 2,6-dichloro-9-benzylpurine, m.p. 152°–152.5° C. and 1.32 g of 2,6-dichloro-7-benzylpurine, m.p. 151°–151.5° C.

PREPARATION B

2-Chloro-6-(1,2,3,4-tetrahydro-6,7-dimethoxy-isooquinol-2-yl)-7-benzylpurine

A mixture of 950 mg of 2,6-dichloro-7-benzylpurine, 780 mg of 1,2,3,4-tetrahydro-6,7-dimethoxyisoquinoline hydrochloride and 700 mg of triethylamine in 80 ml of dimethylacetamide was stirred for 72 hours at room temperature under nitrogen. The reaction mixture was poured into water (300 ml) and the resulting solids filtered, dried and recrystallized from methanol, 1.25 g, m.p. 195°–197° C.

In a similar manner, 1.4 g of 2,6-dichloro-9-benzylpurine gave 1.87 g of 2-chloro-6-(1,2,3,4-tetrahydro-6,7-dimethoxyisoquinol-2-yl)-9-benzylpurine, m.p. 151°–153° C.

PREPARATION C 2,6-Dichloro-7-methylpurine and 2,6-dichloro-9-methylpurine

In a manner similar to Preparation A, 9.52 g of 2,6-dichloropurine, 7.65 g of potassium carbonate and 7.86 g of methyl iodide in 65 ml of dimethylsulfoxide gave 1.54 g of 2,6-dichloro-7-methylpurine and 4.7 g of 2,6-dichloro-9-methylpurine.

PREPARATION D

2-Chloro-6-(1,2,3,4-tetrahydro-6,7-dimethoxyisoquinol-2-yl)-7-methylpurine

A solution of 1.44 g of 2,6-dichloro-7-methylpurine, 1.63 g of 1,2,3,4-tetrahydro-6,7-dimethoxyisoquinoline hydrochloride and 1.5 g of triethylamine in 25 ml of methylene chloride was stirred at room temperature under nitrogen for 15 hours. The reaction mixture was washed with a 1N hydrochloric acid solution (3×150 ml), water (3×150 ml) and a brine solution (1×100 ml), and then dried over sodium sulfate. Removal of the solvent left a residue which was chromatographed on 150 g of silica gel, 1.3 g.

PREPARATION E 2,5-Dichloro-7-(1-phenylethyl)purine and 2,6-dichloro-9-(1-phenylethyl)purine Using the same general procedure of Preparation A, 4.12 g of 2,6-dichloropurine, 3.32 g of potassium carbonate and 4.44 g of 1-bromoethylbenzene gave 830 mg of 2,6-dichloro-7-(1-phenylethyl)purine and 1.3 g of 2,6-dichloro-9-(1-phenylethyl)purine.

PREPARATION F

2-Chloro-6-(1,2,3,4-tetrahydro-6,7-dimethoxyisoquinol-2-yl)-7-(1-phenylethyl)purine Employing the procedure of Preparation B, 730 mg of 2,6-dichloro-7-(1-phenylethyl)purine, 573 mg of 1,2,3,4-tetrahydro-6,7-dimethoxyisoquinoline hydrochloride and 505 mg of triethylamine in 25 ml of dimethylacetamide gave 430 mg of the desired intermediate.

Similarly, 2-Chloro-6-(1,2,3,4-tetrahydro-6,7-dimethoxyisoquinol-2-yl)-9-(1phenylethyl)purine was prepared in 76% yield.

PREPARATION G

2-Chloro-6-(1,2,3,4-tetrahydro-1-[3,4-dimethoxybenzyl]-6,7-dimethoxyisoquinol-2-yl)-9-methylpurine Using the procedure of Preparation D, 2.01 g of 2,6-dichloropurine, 3.76 g of 1,2,3,4-tetrahydro-1-(3,4-dimethoxybenzyl)-6,7-dimethoxyisoquinoline hydrochloride and 4 g of triethylamine in 20 ml of methylene chloride gave 2.31 g of the titled product.

Similarly, 1.42 g of 2,6-dichloro-9obenzylpurine, 1.93 g of 1,2,3,4-tetrahydro-1(3,4-dimethoxybenzyl)-6,7-dimethoxyisoquinoline hydrochloride and 2.12 g of triethylamine in 40 ml of methylene chloride gave 1.98 g of 2-Chloro-6-(1,2,3,4-1-[3,4-dimethoxybenzyl]-6,7-dimethoxyisoquinol-2-yl)-9-benzylpurine.

PREPARATION H 3,5-Dichloro-6,7,8,9-tetrahydrobenzol-[2,3-d]pyrimidine 1. 3,5-dihydroxy-6,7,8,9-tetrahydrobenzo[2,3-d]pyrimidine A mixture of 22.53 g of ethyl 2-amino-4,5,6,7-tetrahydrobenzo[b]thiophene-3-carboxylate and 39.04 g of urea were fused at 180°–190° C. for 3 hours under nitrogen. The mixture was cooled to room temperature and treated with 600 ml of 6N potassium hydroxide solution. The suspension was filtered and the cooled flitrate adjusted to pH 2 with concentrated hydrochloric acid. The precipitated solids were filtered and slurred in refluxing water. The suspension was filtered while hot and the solids dried to give the titled product.

2. 3,5-dichloro-6,7,8,9-tetrahydrobenzo[2,3-d]pyrimidine

The product of Preparation H-1 (4.44 g) was added to 40 ml of phosphorous oxychloride and the reaction mixture refluxed for 72 hours. The reaction was cooled and added carefully to 500 ml of warm water. The cooled mixture was extracted with chloroform (3×500 ml) and the combined extracts washed with water (2×500 ml) and a brine solution (1×300 ml). After drying over sodium sulfate, the solvent was removed in vacuo and the residue chromatographed as the eluent. The fractions containing the product were combined and concentrated. The residue was recrystallized from methanol, m.p. 175°–178° C.

We claim:
1. A compound of the formula

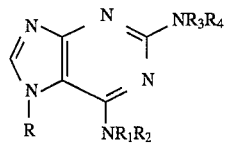

or

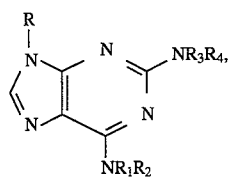

or a pharmaceutically acceptable acid addition salt thereof, wherein R is hydrogen, alkyl having one to three carbon atoms or phenylalkyl having seven to ten carbon atoms; $R_1$ and $R_3$ are each hydrogen or alkyl having one to three carbon atoms;

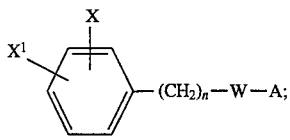

$R_2$ is aralkyl of the formula

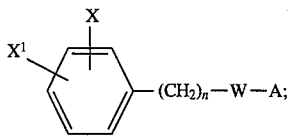

$R_4$ is aralkyl of the formula
where X and $X^1$ for each occurrence are each hydrogen, alkyl having one to three carbon atoms, alkoxy having one to three carbon atoms, hydroxy, fluoro, chloro, trifluoromethyl, amino, alkylamino having one to three carbon atoms or dialkylamino having two to six carbon atoms; or X and $X^1$ taken together are methylenedioxy or ethylenedioxy;
n for each occurrence is an integer of 0 or 1;
W in the definition of $R_2$ is S or O
W in the definition of $R_4$ is S, O or a chemical bond; and
A is alkylene having two to four carbon atoms; and $R_1$ and $R_2$ and
$R_3$ and $R_4$ when taken together with the nitrogen to which they are attached each form a moiety of the formula

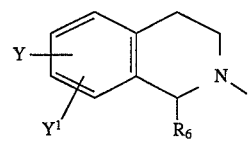

where $R_6$ is hydrogen, alkyl having one to three carbon atoms or dialkoxyphenylalkyl said alkoxy each having one to three carbon atoms and said alkyl having one to three carbon atoms and Y and $y^1$ are each hydrogen, alkyl having one to three carbon atoms, alkoxy having one to three carbon atoms, fluoro, chloro, trifluorom-
ethyl, amino, alkylamino having one to three carbon atoms or dialkylamino having two to six carbon atoms.

2. A compound of claim 1, formula I, where R is phenylalkyl having seven to ten carbon atoms; $R_1$ and $R_2$ taken together with the nitrogen to which they are attached form a moiety of the formula

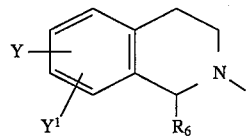

where $R_6$ is hydrogen and Y and $Y^1$ are each alkoxy having one to three carbon atoms; $R_3$ is hydrogen; and $R_4$ is aralkyl of the formula

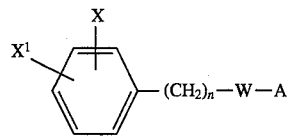

where X and $X^1$ are each alkoxy having one to three carbon atoms, n is 0, W is a chemical bond and A is ethylene.

3. The compound of claim 2, where R is 1-phenylethyl; Y is 6-methoxy and $Y^1$ is 7-methoxy; and X is 3-methoxy and $X^1$ is 4-methoxy.

4. The compound of claim 2, where R is benzyl; Y is 6-methoxy and $Y^1$ is 7-methoxy; and X is 3-methoxy and $X^1$ is 4-methoxy.

5. A compound of claim 1, formula II, where R is alkyl having one to three carbon atoms or phenylalkyl having seven to ten carbon atoms; $R_1$ and $R_2$ taken together with the nitrogen to which they are attached form a moiety of the formula

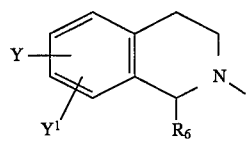

where $R_6$ is hydrogen or dialkoxyphenylalkyl said alkoxy each having one to three carbon atoms and said alkyl having one to three carbon atoms and Y and $Y^1$ are each alkoxy having one to three carbon atoms; $R_3$ is hydrogen; and $R_4$ is aralkyl of the formula

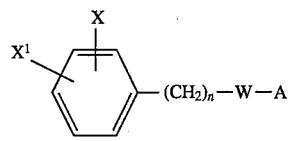

where X and $X^1$ are each alkoxy having one to three carbon atoms, n is 0, W is a chemical bond and A is ethylene.

6. The compound of claim 5, where R is 1-phenylethyl; $R_6$ is hydrogen, Y is 6-methoxy and $Y^1$ is 7-methoxy; and X is 3-methoxy and $X^1$ is 4-methoxy.

7. The compound of claim 5, where R is benzyl; $R_6$ is 3,4-dimethoxybenzyl, Y is 6-methoxy and $Y^1$ is 7-methoxy; and X is 3-methoxy and $X^1$ is 4-methoxy.

8. The compound of claim 5, where R is methyl; $R_6$ is 3,4-dimethoxybenzyl, Y is 6-methoxy and $Y^1$ is 7-methoxy; and X is 3-methoxy and $X^1$ is 4-methoxy.

9. A method of inhibiting a P-glycoprotein in a human suffering from cancer which comprises administering before, with or after the administration to said human of an anticancer effective amount of a chemotherapeutic agent, a P-glycoprotein inhibiting amount of a compound of the formula

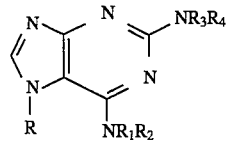

or

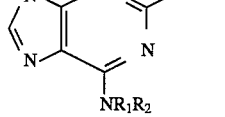

or a pharmaceutically acceptable acid addition salt thereof, wherein R is hydrogen, alkyl having one to three carbon atoms or phenylalkyl having seven to ten carbon atoms; $R_1$ and $R_3$ are each hydrogen or alkyl having one to three carbon atoms; $R_2$ and $R_4$ are each aralkyl of the formula

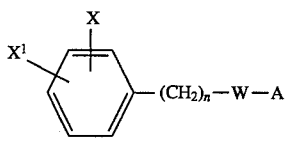

X and $X^1$ are each hydrogen, alkyl having one to three carbon atoms, alkoxy having one to three carbon atoms, hydroxy, fluoro, chloro, trifluoromethyl, amino, alkylamino having one to three carbon atoms or dialkylamino having two to six carbon atoms, X and $X^1$ taken together are methylenedioxy or ethylenedioxy, n is an integer of 0 or 1, W is S, O or a chemical bond and A is alkylene having two to four carbon atoms; and $R_1$ and $R_2$ and $R_3$ and $R_4$ when taken together with the nitrogen to which they are attached each form a moiety of the formula

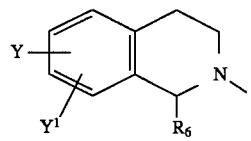

where $R_6$ is hydrogen, alkyl having one to three carbon atoms or dialkoxyphenylalkyl said alkoxy each having one to three carbon atoms and said alkyl having one to three carbon atoms and Y and $y^1$ are each hydrogen, alkyl having one to three carbon atoms, alkoxy having one to three carbon atoms, fluoro, chloro, trifluoromethyl, amino, alkylamino having one to three carbon atoms or dialkylamino having two to six carbon atoms.

10. A pharmaceutical composition for administration to a mammal which comprises a p-glycoprotein inhibiting amount of a compound of the formula

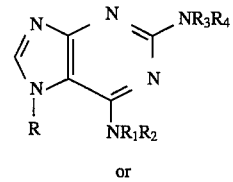

or

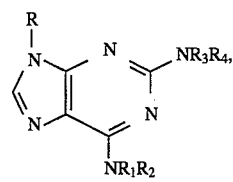

or a pharmaceutically acceptable acid addition salt thereof, wherein R is hydrogen, alkyl having one to three carbon atoms or phenylalkyl having seven to ten carbon atoms; $R_1$ and $R_3$ are each hydrogen or alkyl having one to three carbon atoms; $R_2$ and $R_4$ are each aralkyl of the formula

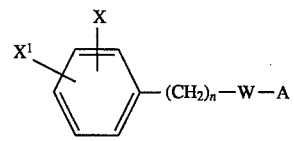

where X and $X^1$ are each hydrogen, alkyl having one to three carbon atoms, alkoxy having one to three carbon atoms, hydroxy, fluoro, chloro, trifluoromethyl, amino, alkylamino having one to three carbon atoms or dialkylamino having two to six carbon atoms, X and $X^1$ taken together are methylenedioxy or ethylenedioxy, n is an integer of 0 or 1, W is S, O or a chemical bond and A is alkylene having two to four carbon atoms; and $R_1$ and $R_2$ and $R_3$ and $R_4$ when taken together with the nitrogen to which they are attached each form a moiety of the formula

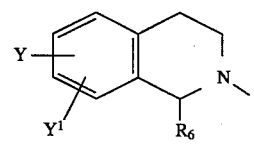

where $R_6$ is hydrogen, alkyl having one to three carbon atoms or dialkoxyphenylalkyl said alkoxy each having one to three carbon atoms and said alkyl having one to three carbon atoms and Y and $Y^1$ are each hydrogen, alkyl having one to three carbon atoms, alkoxy having one to three carbon atoms, fluoro, chloro, trifluoromethyl, amino, alkylamino having one to three carbon atoms or dialkylamino having two to six carbon atoms, a pharmaceutically acceptable carrier and, optionally, an anticancer effective amount of a chemotherapeutic agent.

* * * * *